US00PP25397P2

(12) United States Plant Patent
Goemans

(10) Patent No.: US PP25,397 P2
(45) Date of Patent: Mar. 31, 2015

(54) ***ALSTROEMERIA* PLANT NAMED 'EMILY'**

(50) Latin Name: *Alstroemeria hybrida*
Varietal Denomination: Emily

(71) Applicant: Francis Cornelius Goemans, Chichester (GB)

(72) Inventor: Francis Cornelius Goemans, Chichester (GB)

(73) Assignee: Wulfinghoff Alstroemeria B.V., Rijswijk (NL)

( * ) Notice: Subject to any disclaimer, the term of this patent is extended or adjusted under 35 U.S.C. 154(b) by 146 days.

(21) Appl. No.: 13/815,881

(22) Filed: Mar. 15, 2013

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Susan McCormick Ewoldt
(74) *Attorney, Agent, or Firm* — C. A. Whealy

(57) ABSTRACT

A new and distinct cultivar of *Alstroemeria* plant named 'Emily', characterized by its compact and uniformly mounding plant habit; sturdy and strong plants; vigorous growth habit; large red purple and yellow-colored flowers; and good garden performance.

2 Drawing Sheets

Botanical designation: *Alstroemeria hybrida.*
Cultivar denomination: 'EMILY'.

BACKGROUND OF THE INVENTION

The present invention relates to a new and distinct cultivar of *Alstroemeria* plant, botanically known as *Alstroemeria hybrida*, typically grown as a potted garden *Alstroemeria*, and hereinafter referred to by the name 'Emily'.

The new *Alstroemeria* plant is a product of a planned breeding program conducted by the Inventor in Chichester, United Kingdom. The objective of the breeding program is to create new compact potted *Alstroemeria* plants with uniform plant habit and attractive flower colors.

The new *Alstroemeria* plant originated from a cross-pollination made by the Inventor in Chichester, United Kingdom in June, 2009, of a proprietary selection of *Alstroemeria hybrida* identified as code number T 18, not patented, as the female, or seed, parent with a proprietary *Alstroemeria hybrida* selection identified as code number 390/6, not patented, as the male, or pollen, parent. The new *Alstroemeria* plant was discovered and selected by the Inventor as a flowering plant from within the progeny of the stated cross-pollination in a controlled greenhouse environment in Chichester, United Kingdom in May, 2010.

Asexual reproduction of the new *Alstroemeria* plant by tissue culture in a controlled greenhouse environment in Roelofarendsveen, The Netherlands since October, 2010 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Emily'. These characteristics in combination distinguish 'Emily' as a new and distinct *Alstroemeria* plant:

1. Compact and uniformly mounding plant habit.
2. Sturdy and strong plants.
3. Vigorous growth habit.
4. Large red purple and yellow-colored flowers.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are taller than plants of female parent selection.
2. Plants of the new *Alstroemeria* and female parent selection differ in flower color as plants of female parent selection have mauve-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* are much shorter than plants of the male parent selection.
2. Plants of the new *Alstroemeria* and the male parent selection differ in flower color as plants of the male parent selection have salmon pink-colored flowers.

Plants of the new *Alstroemeria* can be compared to plants of the *Alstroemeria hybrida* 'Davina', disclosed in U.S. Plant Pat. No. 20,703. In side-by-side comparisons conducted in Chichester, United Kingdom, plants of the new *Alstroemeria* differed from plants of 'Davina' in the following characteristics:

1. Plants of the new *Alstroemeria* were larger than plants of 'Davina'.
2. Flowers of plants of the new *Alstroemeria* were more narrow but taller than flowers of plants of 'Davina'.

3. Plants of the new *Alstroemeria* and 'Davina' differed in flower color as plants of 'Davina' had salmon pink and yellow-colored flowers.
4. Plants of the new *Alstroemeria* had longer peduncles than plants of 'Davina'.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Emily' grown in a container.

The photograph on the second sheet is a close-up view of a typical flower of 'Emily'.

DETAILED BOTANICAL DESCRIPTION

The aforementioned photographs and following observations and measurements describe plants of the new *Alstroemeria* grown during the late spring and early summer in 21-cm containers in a glass-covered greenhouse in Chichester, United Kingdom and under cultural practices typical of commercial *Alstroemeria* production. During the production of the plants, day temperatures averaged 20° C. and night temperatures averaged 14° C. Plants were six months old when the photographs and description were taken. Color references are made to The Royal Horticultural Society Colour Chart, 2001 Edition, except where general terms of ordinary dictionary significance are used.

Botanical classification: *Alstroemeria hybrida* 'Emily'.

Parentage:

*Female, or seed, parent*.—Proprietary selection of *Alstroemeria hybrida* identified as code number T 18, not patented.

*Male or pollen parent*.—Proprietary selection of *Alstroemeria hybrida* identified as code number 390/6, not patented.

Propagation:

*Type*.—By tissue culture.

*Root description*.—Medium in thickness; fleshy; color, close to 155A.

*Rooting habit*.—Freely branching; dense.

*Rhizome description*.—Shape: Elongate; rounded. Length: About 4 cm to 8 cm. Diameter: About 6 mm to 13 mm. Texture: Smooth. Color: Close to 155A.

Plant description:

*Plant habit*.—Compact and uniformly mounded; freely branching, dense and bushy appearance; sturdy and strong plants; vigorous growth habit.

*Plant height*.—About 20 cm to 25 cm.

*Plant diameter* (*area of spread*).—About 33 cm.

Stem description:

*Aspect*.—Mostly upright to somewhat outwardly spreading.

*Internode length*.—About 0.5 cm to 3 cm.

*Strength*.—Strong, sturdy.

*Texture*.—Smooth, glabrous.

*Color*.—Close to 144A.

Foliage description:

*Arrangement*.—Alternate; below the peduncles in a single whorl; sessile.

*Length*.—About 6.5 cm.

*Width*.—About 1.6 cm.

*Shape*.—Lanceolate.

*Apex*.—Acute.

*Base*.—Attenuate.

*Margin*.—Entire.

*Texture, upper and lower surfaces*.—Smooth, glabrous.

*Venation pattern*.—Parallel.

*Color*.—Developing and fully expanded leaves, upper surface: Close to 137B; venation, close to 144A. Developing and fully expanded leaves, lower surface: Close to 138B; venation, close to N138B.

Flower description:

*Flower type and habit*.—Single cup-shaped flowers arranged in compound umbels; flowers face mostly upright to outwardly; freely flowering habit; about five to seven flowers per inflorescence; about 30 to 100 flowers developing per plant.

*Natural flowering season*.—Plants begin flowering about 6 to 14 weeks after planting; in the garden, flowering is continuous from the late spring until frost in the United Kingdom.

*Fragrance*.—None detected.

*Flower longevity on the plant*.—About two to three weeks on the plant; about one to two weeks as a cut flower; flowers not persistent.

*Flower buds*.—Length: About 3.1 cm. Diameter: About 1.7 cm. Shape: Ovoid. Color: Close to 64A and 144B.

*Flower diameter*.—About 6.5 cm.

*Flower depth* (*height*).—About 6.7 cm.

*Perianth*.—Arrangement: Six arranged in two whorls, each whorl with two lateral and one median segments. Size, inner perianth: Length, lateral segments: About 4.5 cm. Width, lateral segments: About 1.4 cm. Length, median segment: About 4.2 cm. Width, median segment: About 1.3 cm. Size, outer perianth: Length, lateral segments: About 4.5 cm. Width, lateral segments: About 2.7 cm. Length, median segment: About 4.4 cm. Width, median segment: About 2.7 cm. Shape, inner perianth, all segments: Lanceolate. Shape, outer perianth, all segments: Obovate. Apex, inner perianth, all segments: Cuspidate. Apex, outer perianth, all segments: Emarginate. Base, inner perianth, all segments: Attenuate. Base, outer perianth, all segments: Cuneate. Margin, inner perianth, all segments: Entire to finely crenate. Margin, outer perianth, all segments: Finely crenate. Texture, inner and outer perianths, all segments: Smooth, glabrous. Color, inner perianth: When opening, lateral segments, upper surface: Center, close to 13A; towards the apex and at the base, close to 64A; stripes, close to 183A. When opening, median segment, upper surface: Close to 64A; central spots, close to 13A; stripes, close to 183A. When opening, lateral segments, lower surface: Center, close to 12A; towards the apex, close to 67A; at the base, close to 67A. When opening, median segment, lower surface: Close to 67B. Fully opened, lateral segments, upper surface: Center, close to 13A; towards the apex and at the base, close to 64A; stripes, close to 183A. Fully opened, median segment, upper surface: Close to 64B; central spots, close to 13A; stripes, close to 183A. Fully opened, lateral segments, lower surface: Center, close to 12A; towards the apex, close to 67B; at the base, close to 67B. Fully opened, median segment, lower surface: Close to 67B. Color, outer perianth: When opening, all segments, upper surface: Close to 64A. When opening, all segments, lower surface: Close to 67A. Fully opened, all segments, upper surface: Close to 64B. Fully opened, all segments, lower surface: Close to 67B.

*Peduncles*.—Length: About 12.5 cm. Diameter: About 5 mm. Strength: Strong. Angle: About 30° to 45° from vertical. Texture: Smooth, glabrous. Color: Close to 144A.

*Pedicels*.—Length: About 1.5 cm to 2.5 cm. Diameter: About 2 mm. Strength: Strong. Angle: About 15° to 20° from peduncle axis. Texture: Smooth, glabrous. Color: Close to 144A.

*Reproductive organs*.—Stamens: Quantity per flower: About six. Anther length: About 7 mm. Anther shape: Oval. Anther color: Close to 59B. Pollen amount: Abundant. Pollen color: Close to 199A. Pistils: Quantity per flower: One. Pistil length: About 4 cm. Style length: About 3.5 cm. Style color: Close to 64B. Stigma color: Close to 64B to 64C. Ovary color: Close to 144A.

*Fruits*.—Length: About 1 cm. Diameter: About 7 mm. Color: Close to 143C.

*Seeds*.—Seed development has not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 1° C. to about 25° C.

It is claimed:

1. A new and distinct *Alstroemeria* plant named 'Emily' as illustrated and described.

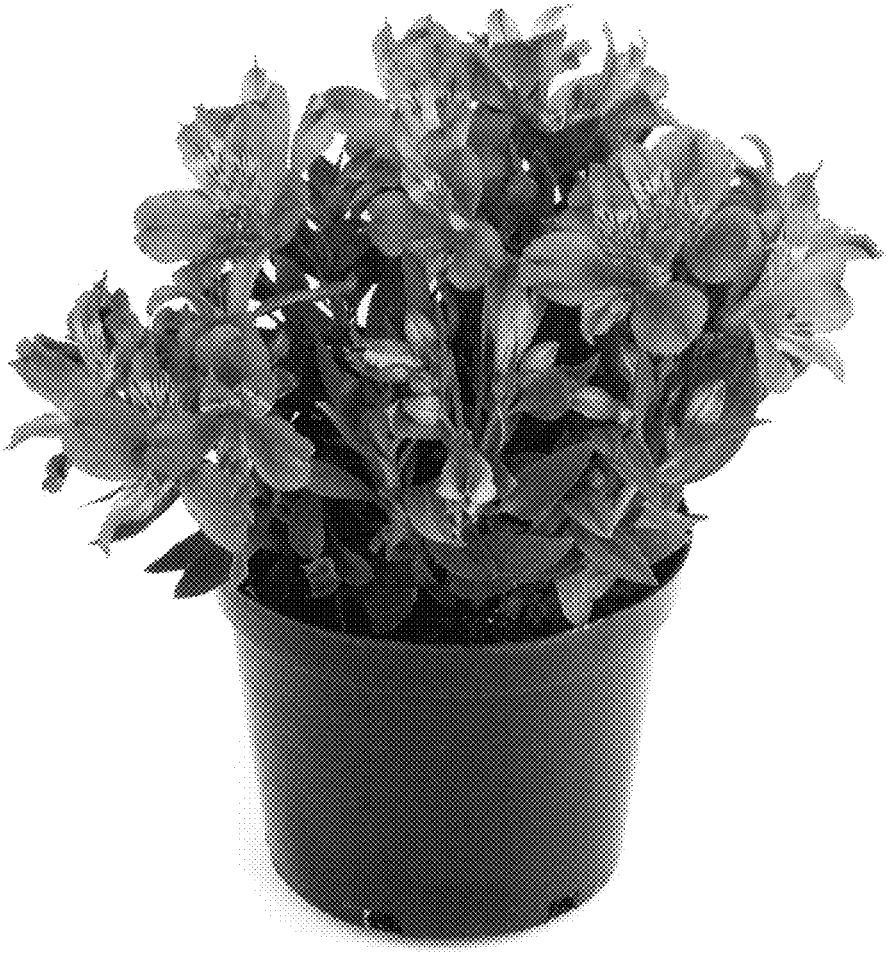

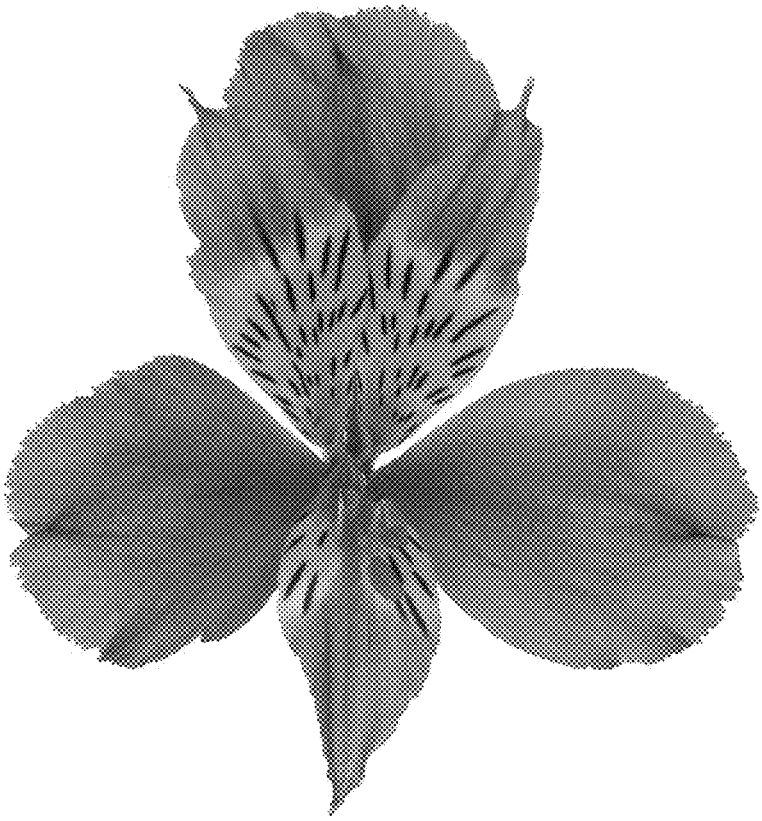

* * * * *